United States Patent
Krebs et al.

(10) Patent No.: US 11,631,500 B2
(45) Date of Patent: Apr. 18, 2023

(54) PATIENT SPECIFIC RISK PREDICTION OF CARDIAC EVENTS FROM IMAGE-DERIVED CARDIAC FUNCTION FEATURES

(71) Applicant: Siemens Healthcare GmbH, Erlangen (DE)

(72) Inventors: Julian Krebs, Moers (DE); Tommaso Mansi, Plainsboro, NJ (US); Bin Lou, Princeton, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 392 days.

(21) Appl. No.: 16/857,306

(22) Filed: Apr. 24, 2020

(65) Prior Publication Data

US 2021/0057104 A1 Feb. 25, 2021

(51) Int. Cl.
| | | |
|---|---|---|
| G06K 9/00 | (2022.01) | |
| G16H 50/30 | (2018.01) | |
| A61B 5/00 | (2006.01) | |
| G16H 30/20 | (2018.01) | |
| G16H 30/40 | (2018.01) | |
| G16H 50/20 | (2018.01) | |
| G16H 50/70 | (2018.01) | |
| A61B 5/024 | (2006.01) | |

(Continued)

(52) U.S. Cl.
CPC ......... *G16H 50/30* (2018.01); *A61B 5/02416* (2013.01); *A61B 5/7267* (2013.01); *A61B 5/7275* (2013.01); *G06F 18/214* (2023.01); *G06V 10/40* (2022.01); *G06V 10/764* (2022.01); *G06V 10/82* (2022.01); *G16H 30/20* (2018.01); *G16H 30/40* (2018.01); *G16H 50/20* (2018.01); *G16H 50/70* (2018.01); *G06V 2201/031* (2022.01)

(58) Field of Classification Search
CPC ........ G16H 50/30; G16H 30/20; G16H 30/40; G16H 50/20; G16H 50/70; A61B 5/02416; A61B 5/7267; A61B 5/7275; A61B 5/0044; G06K 9/6256; G06K 9/627; G06V 10/40; G06V 2201/031; G06V 10/764; G06V 10/82
See application file for complete search history.

(56) References Cited

U.S. PATENT DOCUMENTS

| | | | |
|---|---|---|---|
| 8,668,644 B2 * | 3/2014 | Ong | A61B 5/14542 600/509 |
| 9,179,881 B2 * | 11/2015 | Menon Gopalakrishna | A61B 8/463 |

(Continued)

OTHER PUBLICATIONS

Rijnierse et al., "Usefulness of Left Atrial Emptying Fraction to Predict Ventricular Arrhythmias in Patients With Implantabable Cardioverter Defibrillators", Am J Cardiol, 2017, vol. 120, pp. 243-250.

(Continued)

*Primary Examiner* — Shervin K Nakhjavan

(57) ABSTRACT

Systems and methods for predicting a patient specific risk of cardiac events for cardiac arrhythmia are provided. A medical image sequence of a heart of a patient is received. Cardiac function features are extracted from the medical image sequence. Additional features are extracted from patient data of the patient. A patient specific risk of a cardiac event is predicted based on the extracted cardiac function features and the extracted additional features.

16 Claims, 5 Drawing Sheets

(51) Int. Cl.
*G06V 10/40* (2022.01)
*G06F 18/214* (2023.01)
*G06V 10/764* (2022.01)
*G06V 10/82* (2022.01)

(56) References Cited

U.S. PATENT DOCUMENTS

| | | | | |
|---|---|---|---|---|
| 2005/0234355 | A1* | 10/2005 | Rowlandson | A61B 5/349 600/509 |
| 2007/0273504 | A1* | 11/2007 | Tran | A61B 5/7405 340/539.12 |
| 2010/0280352 | A1* | 11/2010 | Ionasec | G06N 7/005 600/407 |
| 2011/0166618 | A1* | 7/2011 | Zhang | A61N 1/37258 607/28 |
| 2011/0224962 | A1* | 9/2011 | Goldberger | G16H 50/50 703/11 |
| 2011/0257545 | A1* | 10/2011 | Suri | A61B 8/5223 600/508 |
| 2012/0022843 | A1* | 1/2012 | Ionasec | G06T 13/20 703/11 |
| 2015/0042646 | A1* | 2/2015 | Comaniciu | G06T 7/12 345/420 |
| 2015/0164453 | A1* | 6/2015 | Choi | A61B 6/032 600/407 |
| 2016/0058520 | A1* | 3/2016 | Yang | A61B 34/10 703/11 |
| 2017/0235915 | A1* | 8/2017 | Mansi | G16H 50/30 705/3 |
| 2017/0255745 | A1* | 9/2017 | Mihalef | G16H 50/50 |
| 2018/0116725 | A1* | 5/2018 | Ashikaga | A61B 5/7275 |
| 2018/0147305 | A1* | 5/2018 | Provost | A61B 6/037 |
| 2020/0111210 | A1* | 4/2020 | Maximo | G06T 7/0014 |
| 2020/0185084 | A1* | 6/2020 | Syeda-Mahmood | A61B 8/5223 |
| 2021/0059612 | A1* | 3/2021 | Krebs | A61B 5/7267 |
| 2021/0137384 | A1* | 5/2021 | Robinson | G06T 7/0012 |
| 2021/0350179 | A1* | 11/2021 | Bello | G06N 3/0454 |

OTHER PUBLICATIONS

Negishi et al., "Left atrial booster pump function is an independent predictor of subsequent life-threatening ventricular arrhythmias in non-ischaemic cardiomyopathy", Eur Heart J Cardiovasc Imaging, 2016, vol. 17, pp. 1153-1160.

Habibi et al., "The association of baseline left atrial structure and function measured with cardiac magnetic resonance and pulmonary vein isolation outcome in patients with drug-refractory atrial fibrillation", Heart Rhythm Society, 2016, vol. 13, pp. 1037-1044.

Kobayashi et al., "Assessment of atrial synchrony in paroxysmal atrial fibrillation and impact of pulmonary vein isolation for atrial dyssynchrony and global strain by three-dimensional strain echocardiography", J Am Soc Echocardiogr, 2014, vol. 27, No. 11, pp. 1193-1199.

Lou et al., "An image-based deep learning framework for individualising radiotherapy dose: a retrospective analysis of outcome prediction", www.thelancet.com/digital-health, 2019, vol. 1, Jul. 2019, pp. e136-e147.

Krebs et al., "Probabilistic Motion Modeling from Medical Image Sequences: Application to Cardiac Cine-MRI", STACOM 2019: Statistical Atlases and Computational Models of the Heart, Oct. 2019, arXiv:1907.13524v2, Sep. 2019, pp. 1-10.

Ganesan et al., "Long-term outcomes of catheter ablation of atrial fibrillation: a systematic review and meta-analysis", Journal of the American Heart Association, 2013, 1-14 pgs.

* cited by examiner

PATIENT SPECIFIC RISK PREDICTION OF CARDIAC EVENTS FROM IMAGE-DERIVED CARDIAC FUNCTION FEATURES

CROSS-REFERENCE TO RELATED APPLICATIONS

This application claims the benefit of U.S. Provisional Application No. 62/889,195, filed Aug. 20, 2019, the disclosure of which is incorporated herein by reference in its entirety.

TECHNICAL FIELD

The present invention relates generally to patient specific risk prediction of cardiac events, and in particular to patient specific risk prediction of cardiac events for cardiac arrhythmia from image-derived cardiac function features and other multi-modal features.

BACKGROUND

Cardiac arrhythmia is a condition in which the heart rate of a patient is irregular. A heart rate that is too fast is referred to as tachycardia while a heart rate that is too slow is referred to as bradycardia. While most types of cardiac arrhythmia do not pose serious risks, some cardiac arrhythmias may cause major implications, such as stroke, heart failure, or death. Accordingly, one important task is predicting risk of cardiac events for patients exhibiting symptoms of cardiac arrhythmia.

In current clinical practice, cardiac arrhythmia is typically treated following standard global rules, resulting in an overly broad selection of patients treated invasively. For example, patients with atrial fibrillation (AF), the most common type of cardiac arrhythmia in humans, are typically treated with catheter ablation. However, catheter ablation is associated with a high recurrence rate after ablation due to insufficient patient selection.

One commonly used tool for measuring the predictiveness of certain features on events is the Cox proportional-hazards model. Using univariate and multivariate Cox models, certain cardiac functional and structural features, such as the left atrium function and left atrium volume, have been found to be associated with different types of cardiac arrhythmia. While such features have clear physical meaning, such Cox models do not take into account all of the underlying features that exist in medical images and other clinical data that are useful as risk predictors for future cardiac arrhythmias.

BRIEF SUMMARY OF THE INVENTION

In accordance with one or more embodiments, systems and methods for predicting a patient specific risk of a cardiac event for cardiac arrhythmia are provided. A medical image sequence of a heart of a patient is received. Cardiac function features are extracted from the medical image sequence. Additional features are extracted from patient data of the patient. A patient specific risk of a cardiac event is predicted based on the extracted cardiac function features and optionally the extracted additional features.

In one embodiment, the patient specific risk of the cardiac event may be predicted by determining a risk score representing the patient specific risk of the cardiac event. The patient specific risk of the cardiac event may be classified based on the risk score.

In one embodiment, the cardiac function features are extracted from the medical image sequence by encoding pairs of images of the medical image sequence into the cardiac function features using a machine learning based feature extractor network. The additional features are extracted from the patient data of the patient by encoding the patient data of the patient into additional features using one or more additional machine learning based feature extractor networks. The patient specific risk of the cardiac event is predicted by concatenating the cardiac function features and the additional features to form a feature vector and encoding the feature vector to features representing the patient specific risk of cardiac events using a machine learning based risk regression network. The machine learning based feature extractor network, the one or more additional machine learning based feature extractor networks, and the machine learning based risk regression network may be individually trained or trained together.

These and other advantages of the invention will be apparent to those of ordinary skill in the art by reference to the following detailed description and the accompanying drawings.

DETAILED DESCRIPTION

The present invention generally relates to methods and systems for patient specific risk prediction of a cardiac event from image-derived cardiac function features. Embodiments of the present invention are described herein to give a visual understanding of such methods and systems. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Embodiments described herein utilize underlying features extracted from medical imaging data and other multi-modal sources of patient data for predicting a patient specific risk of a cardiac event. The patient specific risk of the cardiac event may be for cardiac arrhythmia or any other cardiac condition (e.g., heart failure). A cardiac event includes any medical event associated with the heart of a patient, such as, e.g., outcomes of treatment associated with the heart, occurrence or recurrence of a major adverse cardiovascular event (MACE), or any other event associated with the heart.

Advantageously, the patient specific risk of a cardiac event is predicted in accordance with embodiments described herein utilizing more features extracted from medical images and other patient or clinical data as compared to conventional approaches, resulting in a more accurate and improved patient specific prediction of risk of a cardiac event.

It should be understood that while embodiments described herein are described with respect to the predicting risk of cardiac events for cardiac arrhythmias, such embodiments are not so limited. Embodiments may be applied for predicting risk of cardiac events for any disease associated with the heart of a patient.

Figure 1:
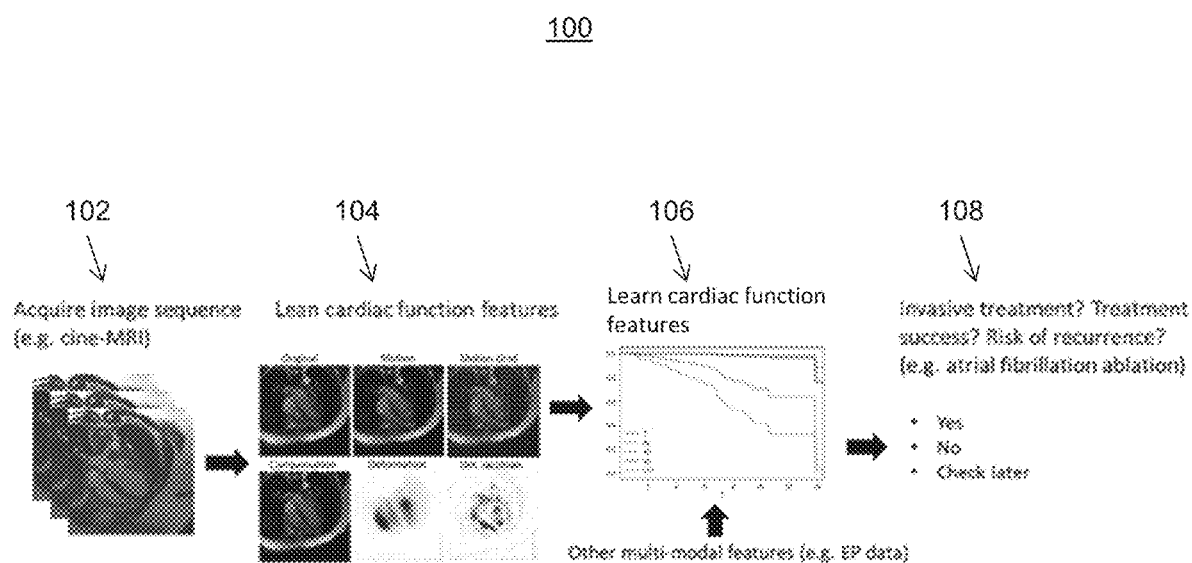
FIG. 1 shows a framework for predicting a patient specific risk of a cardiac event for a patient, in accordance with one or more embodiments.

FIG. 1 shows a framework 100 for predicting a patient specific risk of a cardiac event, in accordance with one or more embodiments. At step 102, a medical image sequence is acquired. The medical image sequence may be a cine-MRI (magnetic resonance imaging) image sequence or an image sequence of any other suitable modality (e.g., ultrasound or computer tomographic images). At step 104, cardiac function features are learned from the image sequence. Exemplary cardiac function features are represented in framework 100 as features of the original image sequence, motion features, motion grid features, compensation features deformation features, and Jacobian determination features. At step 106, a patient specific risk of cardiac events is predicted using the cardiac function features and, optionally, other multi-modal features, such as, e.g., electrophysiological (EP) data. At step 108, the patient specific risk of cardiac events is classified. The classification may comprise, for example, a classification of risk associated with an invasive treatment, the risk associated with success of a treatment, and the risk of recurrence of a cardiac event.

Figure 2:
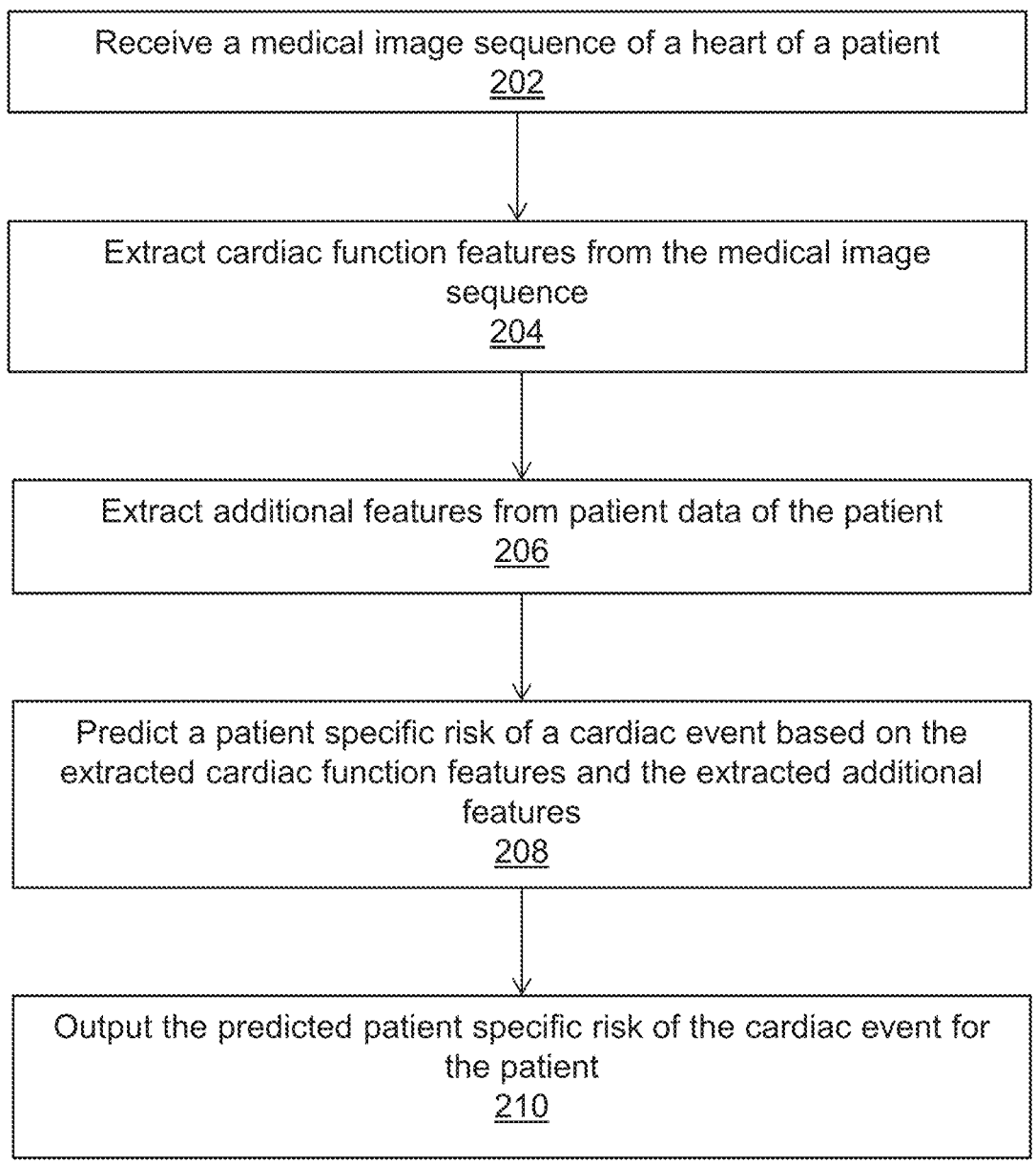
FIG. 2 shows a method for predicting a patient specific risk of a cardiac event, in accordance with one or more embodiments.

FIG. 2 is a method 200 for predicting a patient specific risk of a cardiac event, in accordance with one or more embodiments. Method 200 of FIG. 2 will be described with continued reference to FIG. 1. The steps of method 200 may be performed by one or more suitable computing devices, such as computer 502 of FIG. 5.

At step 202, a medical image sequence of a heart of a patient is received. In one example, the medical image sequence may be the medical image sequence acquired at step 102 of FIG. 1. The medical image sequence may be a time sequence of medical images (or frames) showing dynamic motion of the heart of the patient. In one embodiment, the medical image sequence is a cine-MRI image sequence. However, the medical image sequence may be acquired using any suitable imaging modality. For example, the medical image sequence may be a sequence of MR images, cine-MRI images, computed tomography (CT) images, echocardiogram images, x-ray images, or medical images acquired using any other medical imaging modality or combinations of medical imaging modalities. The medical image sequence may be a sequence of 2D medical images or 3D medical volumes. The medical image sequence may be received directly from an image acquisition device, such as an MR scanner, CT scanner, ultrasound scanner, etc., as the medical image sequence of the patient is acquired, or can be received by loading a previously acquired medical image sequence of the patient from a storage or memory of a computer system or receiving a medical image that has been transmitted from a remote computer system.

At step 204, cardiac function features are extracted from the medical image sequence. In one example, the cardiac function features are the cardiac function features learned at step 104 of FIG. 1. The cardiac function features are low dimensional features extracted from the medical image sequence that relate to cardiac function. The cardiac function features may include features of the original medical image sequence, motion features, motion grid features, compensation features, deformation features, Jacobian determination features, or any other suitable feature.

The cardiac function features may be extracted from pairs of images in the medical image sequence using a trained machine learning based feature extractor. The feature extractor may be an encoder network, such as the encoder networks shown and described with respect to FIGS. 3 and 4. Image pairs of the medical image sequence are input into the encoder network and each image pair is separately encoded by the encoder network into respective cardiac function features. In one embodiment, each image pair comprises moving image $I_0$ and a respective fixed image $I_t$ of the medical image sequence having T+1 frames, where t∈[1, T+1]. The encoder network may be trained during a prior offline or training stage, together with a decoding network, as shown and described with respect to FIG. 3 below. In one embodiment, feature extractor is the encoder network of the motion model described in U.S. patent application Ser. No. 16/834,269, filed Mar. 30, 2020, the disclosure of which is herein incorporated by reference in its entirety.

Figure 3:
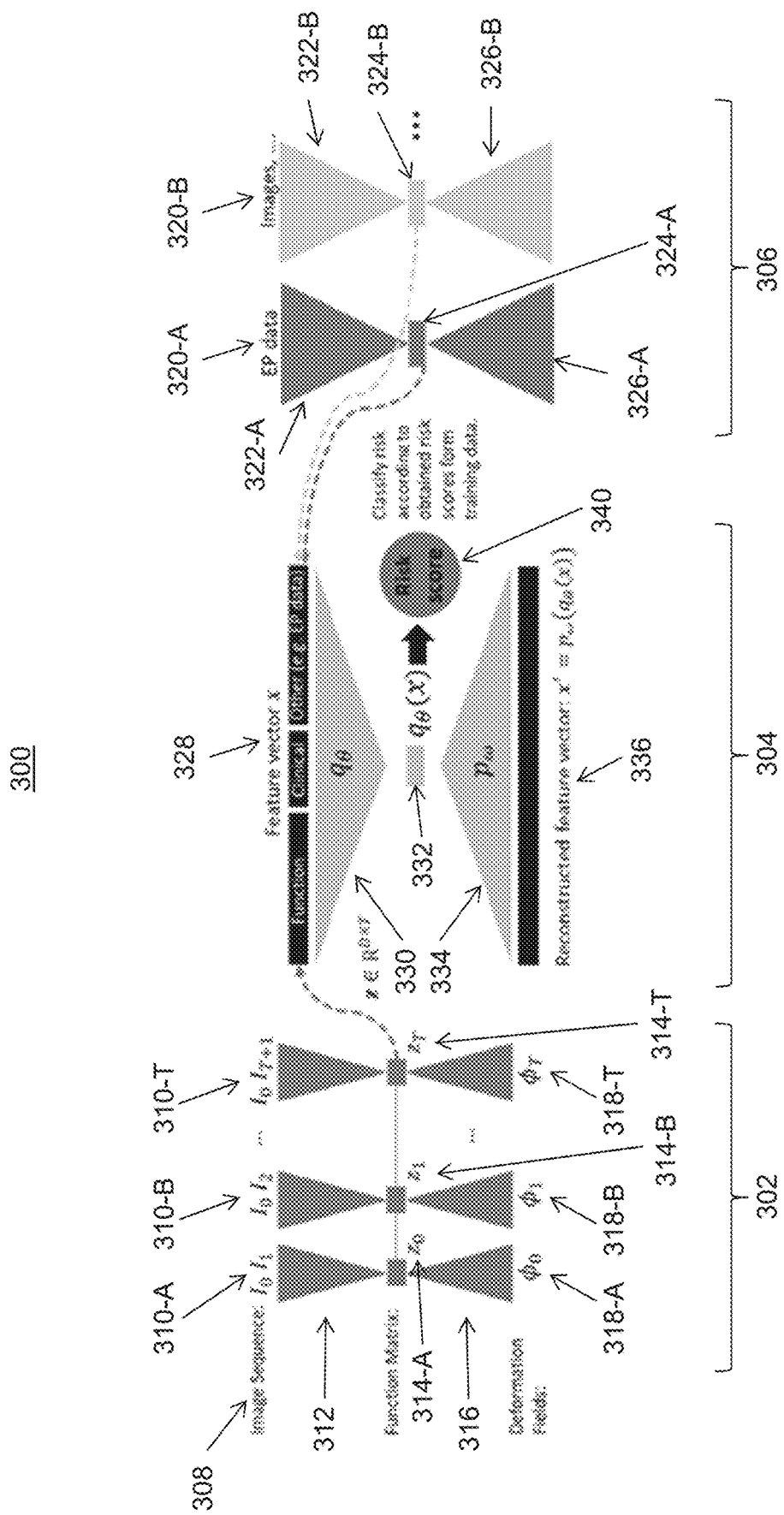
FIG. 3 shows a framework for training a plurality of machine learning networks for predicting a patient specific risk of a cardiac event, in accordance with one or more embodiments.

At step 206, optionally, additional features are extracted from patient data of the patient. In one example, the additional features are the other multi-modal features used to predict risk at step 106 of FIG. 1. The additional features may be extracted from patient data of the patient, such as, e.g., EP data (e.g., echocardiograms or invasive anatomical maps), images, meshes, or clinical data (e.g., blood analytics or patient characteristics) of the patient. The additional features may be extracted from patient data using one or more feature extractors, such as, e.g., one or more of the feature extractors shown and described with respect to FIGS. 3 and 4. Such feature extractors extract expressive low dimensional features from high-dimensional patient data. The feature extractors may be selected based on the type of patient data from which the additional features are extracted. The feature extractors are trained during a prior offline or training stage, as shown and described with respect to FIG. 3 below At step 208, a patient specific risk of a cardiac event is predicted based on the extracted cardiac function features and, optionally, the extracted additional features and other low dimensional clinical data. The extracted cardiac function features, the extracted additional features, and the other low dimensional clinical data are concatenated into a feature vector and the feature vector is input into a machine learning based risk regression network. In one embodiment, the risk regression network is an encoder network of a task-specific autoencoder, such as shown in FIG. 3. A risk regression network is trained for the cardiac event (e.g., atrial fibrillation recurrence, deadly arrhythmia, etc.) during a prior offline or training stage, together with a decoding network, as shown and described with respect to FIG. 3 below.

The risk regression network encodes the feature vector into low dimensional features representing a risk score for the cardiac event, such as, e.g., treatment outcomes, occurrence or recurrence, etc. In one embodiment, the risk of cardiac events may be classified based on the risk score. For example, the classification may be a decision (e.g., yes, no, or check later) to treat (e.g., invasively) the patient based on the risk score, a level of risk (e.g., high, medium, or low) associated with treatment of the patient, a level of risk associated with occurrence or recurrence of a cardiac event (e.g., after treatment), or any other classification. The classification may be determined by comparing the risk score to one or more thresholds. The prediction of cardiac arrhythmia may include the risk score and the classification.

The risk score is defined by the logarithm of the hazard ratio as typical assumed in the Cox regression analysis. As described with respect to FIG. 3 below, the risk regression network is trained using the negative log partial likelihood as the survival function over censored training samples comprising future event data. To this end, the risk regression network represents a non-linear version of the Cox survival analysis.

In one embodiment, for example if the dimensionality of the patient data is not high, the patient data may be directly concatenated with the extracted cardiac function features and the other low dimensional clinical data without performing step 206.

At step 210, the predicted patient specific risk of a cardiac event (e.g., the risk score and/or the classification) is output. For example, the predicted patient specific risk of a cardiac event can be output by displaying the predicted patient specific risk of a cardiac event on a display device of a computer system, storing the predicted patient specific risk of a cardiac event on a memory or storage of a computer system, or by transmitting the predicted patient specific risk of a cardiac event to a remote computer system.

Advantageously, the patient specific risk of a cardiac event predicted in accordance with embodiments described herein is significantly improved by using task-specific cardiac function features and other multi-modal features, as compared with conventional approaches that only use a few manually extracted features. Embodiments described herein utilize high-dimensional multi-modal patient data (e.g., EP data, images, etc.) to thereby use more features for risk prediction. The cumbersome process of extracted handcrafted features, such as left atrium string is not required in accordance with embodiments described herein. Such advantages of embodiments described herein are realized, in part, by applying different neural networks trained as task-specific feature extractors for extracting cardiac function features at step 204, extracting additional features at step 206, and predicting a patient specific risk of cardiac events at step 208. Besides optional clinical features, only task-specific features (i.e., the cardiac function features and the additional features) are used for risk prediction, in accordance with embodiments described herein.

In one use case, embodiments described herein may be implemented in a cardiology system to provide a risk estimation of future cardiac arrhythmias to support physician decision-making for or against an invasive treatment (e.g., AF ablation). A probabilistic motion model may be learned to extract cardiac function features. The cardiac function features, and optionally additional features from other multi-modal data sources, are input into a non-linear risk regression model to predict the risk of future cardiac arrhythmias. In an end-to-end training, all networks can be trained in a task-specific way such that features are optimally suited for the risk estimation task.

FIG. 3 shows a framework 300 for training a plurality of machine learning networks for predicting a patient specific risk of cardiac events, in accordance with one or more embodiments. Framework 300 comprises network 302 for extracting cardiac function features, one or more networks 306 for extracting additional features, and network 304 for predicting a patient specific risk of cardiac events. Networks 302, 304, and 306 may be autoencoders each comprising an encoder network and a decoder network. In particular, network 302 comprises encoder network 312 and decoder network 316. Networks 306 comprise encoder networks 322-A, 322-B, . . . (collectively referred to as encoder networks 322) and decoder networks 326-A, 326-B, . . . (collectively referred to as decoder networks 326). Network 304 comprises encoder network 330 and decoder network 334.

Networks 302, 306 and 304 are trained during a prior offline or training stage using respective encoder networks 312, 322, and 330 and respective decoder networks 316, 326, and 334 according to framework 300. Once trained, networks 302, 306, and 304 are applied during an online or inference stage using respective encoder networks 312, 322, and 330. For example, encoder network 312 may be applied at step 204 of FIG. 2 to extract the cardiac function features, encoder networks 322 may be applied at step 206 of FIG. 2 to extract the additional features, and encoder network 330 may be applied at step 208 of FIG. 2 to determine a patient specific prediction of cardiac arrhythmia. Decoder networks 316, 326, and 334 are only used during the training stage in order to constrain and regularize respective encoder networks 312, 322, and 330 to avoid-overfitting and are not used during the inference stage.

Network 302 comprises encoder network 312 and decoder network 316. Encoder network 312 receives training image pairs 310-A, 310-B, . . . , 310-T (collectively referred to as training image pairs 310) of training medical image sequence 308 having T+1 frames. Each training image pair 310 comprises moving image $I_0$ and a respective fixed image $I_t$ of the training medical image sequence, where $t \in [1, T+1]$. Encoder network 312 independently encodes each training image pairs 310 into respective cardiac function features $z_0$ 314-A, $z_1$ 314-B, . . . , $z_T$ 314-T (collectively referred to as cardiac function features $z_t$ 314), collectively forming function matrix $z \in R^{D \times T}$. Cardiac function features 314 are low dimensional features extracted from training image pairs 310 that relate to cardiac function. Exemplary features include features of the original images, motion features, motion grid features, compensation features, deformation features, Jacobian determination features, or any other suitable feature. Decoder network 316 determines respective deformation fields $\phi_0$ 318-A, $\phi_1$ 318-B, . . . , $\phi_T$ 318-T (collectively referred to as deformation fields $\phi_t$ 314) from cardiac function features $z_t$ 314. Deformation fields $\phi_t$ 318 represent motion between the training image pairs 310 and may be diffeomorphic. Deformation fields $\phi_t$ 318 may be applied by decoder network 316 to transform moving image $I_0$ to reconstruct respective fixed images $I_t$. Accordingly, network 302 is trained to perform a temporal registration of the moving image $I_0$ with each fixed image $I_t$. Network 302 may be trained using any suitable loss function.

Figure 4:
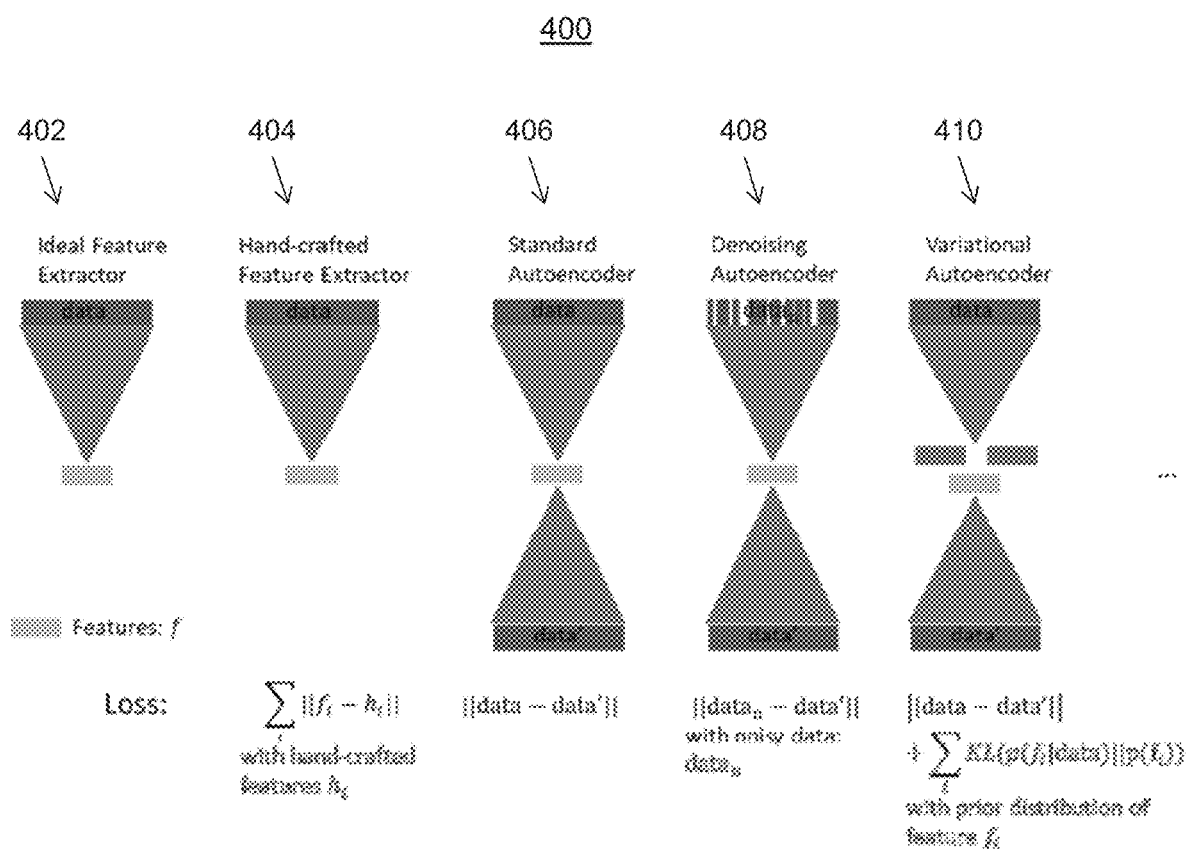
FIG. 4 shows a plurality of exemplary neural networks that may be used to implement one or more feature extractor networks described herein, in accordance with one or more embodiments.

Networks 306 include a network for each type of training patient data from which additional features are to be extracted. The architecture of each of the networks 306 is based on the type of the patient data. Such training patient data may comprise EP data 320-A (e.g., echocardiograms invasive-anatomical maps) and images 320-B (collectively referred to as training patient data 320). Training patient data 320 may additionally or alternatively include any other type of patient data, such as, e.g., meshes, blood analytics, patient characteristics, etc. As shown in framework 300, encoder networks 322-A and 322-B respectively encode EP data 320-A and images 320-B into low dimensional features 324-A and 324-B (collectively referred to as additional features 324). Decoder networks 326-A and 326-B respectively reconstruct EP data 320-A and images 320-B from features 324-A and 324-B. Networks 306 may be trained using any suitable reconstruction loss function, such as, e.g., mean-of-squared differences between the input and the output with a regularizer on the distribution of the features. Any other suitable reconstruction loss function may also be applied, such as, e.g., reconstruction loss functions typically utilized for training autoencoders, denoising autoencoders, variational autoencoders, etc. FIG. 4 describes various architectures and loss functions on which networks 306 may be configured and trained, in accordance with one embodiment.

Network 304 comprises encoder network 330 and decoder network 334. Network 304 may be a non-linear risk regression model formed by a task-specific autoencoder, which learns an optimized latent representation for risk prediction based on observed cardiac events. Network 304 is trained for a particular cardiac event using training data for the particular cardiac event, and may be retrained for other cardiac events. The risk regression model may comprise multiple dense network layers. Encoder network 330 encodes feature vector x 328 into low dimensional features 332. Feature vector x 328 comprises a concatenation of cardiac function features 314, additional features 324, and other training clinical features. Decoder network 334 decodes features 332 to reconstruct feature vector x 328 as reconstructed feature vector x' 336 as. Features 332 represent a patient specific risk score 340 of cardiac events. The risk of cardiac events may be classified based on risk score 340 using one or more thresholds. For example, the classification may include a decision for treatment (e.g., yes, no, check later), the level of risk (e.g., high, medium, or low) associated with treatment, the level of risk of occurrence or recurrence of a cardiac event, or any other classification. The classification may be determined by comparing the risk score to one or more thresholds.

In one embodiment, network 304 is trained with loss function $\mathcal{L}$ using a feature reconstruction loss term $\mathcal{L}_{rec}$ combined with a supervised Cox survival loss term $\mathcal{L}_{risk}$, as defined in Equation (1):

$$\mathcal{L} = \mathcal{L}_{rec} + \gamma \mathcal{L}_{risk} \quad \text{Equation (1)}$$

where feature reconstruction loss term $\mathcal{L}_{rec}$ and supervised Cox survival loss term $\mathcal{L}_{risk}$ are respectively defined in Equations (2) and (3):

$$\mathcal{L}_{rec} = \frac{1}{N} \sum_{i=1}^{N} \|x_i - p_\omega(q_\theta(x_i))\|^2 \quad \text{Equation (2)}$$

$$\mathcal{L}_{risk} = -\sum_{i=1}^{N} \delta_i \left[ q_\theta(x_i) - \log \sum_{j=1}^{N} R_{ij} \exp(q_\theta(x_i)) \right] \quad \text{Equation (3)}$$

Using censoring indicator $\delta_i=1$ if event and $\delta_i=0$ if censored, risk matrix $R_{ij}=1$ if $t_j \geq t_i$ and $R_{ij}=0$ if $t_j < t_i$, based on N samples per batch. This represents a non-linear Cox proportional hazard model where the risk score obtained from the $r=q_\theta(x_i)$ network 304 is defined by the logarithm of the hazard ratio as typically assumed in the Cox regression analysis.

In one embodiment, network 304 is trained for a plurality of cardiac events to predict a general risk score for the plurality of cardiac events.

In accordance with one embodiment, networks 302, 304, and 306 are individually trained using training data comprising training image sequences and other patient and/or clinical data for a patient cohort with known future cardiac events. First, network 302 is trained using the training data in an unsupervised manner to obtain cardiac function features and networks 306 are trained using the training data to obtain the additional features. Networks 302 and 306 may be trained sequentially in any order or in parallel. Next, network 304 is trained to extract features representing the risk score based on observed outcomes in the training data using the extracted cardiac function features extracted by the trained network 302 and the additional features extracted by the trained network 306. One or more thresholds are determined based on risk scores in the training data to classify the risk.

In accordance with another embodiment, networks 302, 304, and 306 are collectively trained together in an end-to-end manner. In end-to-end training, network 304 is trained according to Equation (1) by extending loss function $\mathcal{L}$ by weighted summands of all feature extract loss terms from networks 302 and 206. One advantage of end-to-end training of networks 302, 304, and 306 is that networks 302 and 306 are trained to extract task-specific features that are optimized for risk prediction. However, end-to-end training comes with higher training costs. In particular, networks 302 and 306 are expensive to train due to the high dimensionality of the input data, which may be images or image sequences (with potentially millions of parameters). According, training networks 302 and 306 may take a significant amount of time (e.g., up to 24 hours). Network 304 may be trained more efficiently (e.g., a few minutes) since the input features have relatively low dimensionality (e.g., a few hundred or thousand input parameters).

In accordance with another embodiment, networks 302, 304, and 306 are trained using a combination of individual training and end-to-end training by pre-training some of networks 302 and/or 306, while training the remaining networks in an end-to-end manner with network 304.

FIG. 4 shows a plurality of exemplary neural networks 400 that may be used to implement one or more of the feature extractor networks described herein, in accordance with one or more embodiments. Neural networks 400 may be applied to learn cardiac function features at step 104 of FIG. 1 or extract multi-modal features used at step 106 of FIG. 1, applied to extract cardiac function features at step 204 of FIG. 2 or extract additional features at step 206 of FIG. 2, or may be networks 302 or 306 of FIG. 3. One or more of the plurality of neural networks 400 may be used based on the type of data from which features are to be extracted. As shown in FIG. 4, the plurality of neural networks comprise an idea feature extractor 402, a hand-crafted feature extractor 404 trained with loss function $\Sigma_i\|f_i-h_i\|$ using hand-crafted features $h_i$, a standard autoencoder 406 trained with loss function $\|data-data'\|$, a denoising autoencoder 408 trained with loss function $\|data_n-data'\|$ using noisy data $data_n$, and a variational autoencoder 410 trained with loss function $\|data-data'\|+\Sigma_i KL(p(f_i|data)\|p(f_i))$ using prior distribution of features $p(f_i)$.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the steps or functions of the methods and workflows described herein, including one or more of the steps or functions of FIGS. 1-2. Certain steps or functions of the methods and workflows described herein, including one or more of the steps or functions of FIGS. 1-2, may be performed by a server or by another processor in a network-based cloud-computing system. Certain steps or functions of the methods and workflows described herein, including one or more of the steps of FIGS. 1-2, may be performed by a client computer in a network-based cloud computing system. The steps or functions of the methods and workflows described herein, including one or more of the steps of FIGS. 1-2, may be performed by a server and/or by a client computer in a network-based cloud computing system, in any combination.

Systems, apparatus, and methods described herein may be implemented using a computer program product tangibly embodied in an information carrier, e.g., in a non-transitory machine-readable storage device, for execution by a programmable processor; and the method and workflow steps described herein, including one or more of the steps or functions of FIGS. 1-2, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 5:
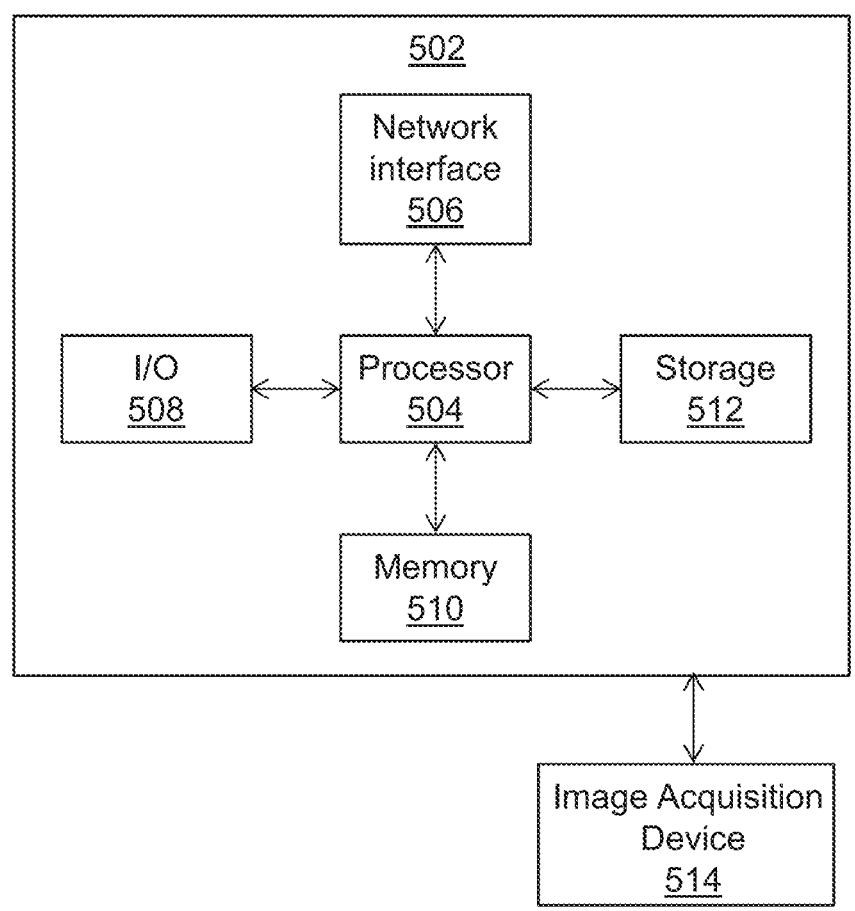
FIG. 5 shows a high-level block diagram of a computer.

A high-level block diagram of an example computer 502 that may be used to implement systems, apparatus, and methods described herein is depicted in FIG. 5. Computer 502 includes a processor 504 operatively coupled to a data storage device 512 and a memory 510. Processor 504 controls the overall operation of computer 502 by executing computer program instructions that define such operations. The computer program instructions may be stored in data storage device 512, or other computer readable medium, and loaded into memory 510 when execution of the computer program instructions is desired. Thus, the method and workflow steps or functions of FIGS. 2-4 can be defined by the computer program instructions stored in memory 510 and/or data storage device 512 and controlled by processor 504 executing the computer program instructions. For example, the computer program instructions can be implemented as computer executable code programmed by one skilled in the art to perform the method and workflow steps or functions of FIGS. 2-4. Accordingly, by executing the computer program instructions, the processor 504 executes the method and workflow steps or functions of FIGS. 2-4. Computer 502 may also include one or more network interfaces 506 for communicating with other devices via a network. Computer 502 may also include one or more input/output devices 508 that enable user interaction with computer 502 (e.g., display, keyboard, mouse, speakers, buttons, etc.).

Processor 504 may include both general and special purpose microprocessors, and may be the sole processor or one of multiple processors of computer 502. Processor 504 may include one or more central processing units (CPUs), for example. Processor 504, data storage device 512, and/or memory 510 may include, be supplemented by, or incorporated in, one or more application-specific integrated circuits (ASICs) and/or one or more field programmable gate arrays (FPGAs).

Data storage device 512 and memory 510 each include a tangible non-transitory computer readable storage medium. Data storage device 512, and memory 510, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 508 may include peripherals, such as a printer, scanner, display screen, etc. For example, input/output devices 508 may include a display device such as a cathode ray tube (CRT) or liquid crystal display (LCD) monitor for displaying information to the user, a keyboard, and a pointing device such as a mouse or a trackball by which the user can provide input to computer 502.

An image acquisition device 514 can be connected to the computer 502 to input image data (e.g., medical images) to the computer 502. It is possible to implement the image acquisition device 514 and the computer 502 as one device. It is also possible that the image acquisition device 514 and the computer 502 communicate wirelessly through a network. In a possible embodiment, the computer 502 can be located remotely with respect to the image acquisition device 514.

Any or all of the systems and apparatus discussed herein, including networks 302, 304, and 306, may be implemented using one or more computers such as computer 502.

One skilled in the art will recognize that an implementation of an actual computer or computer system may have other structures and may contain other components as well, and that FIG. 5 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method comprising:
   receiving a medical image sequence of a heart of a patient;
   extracting cardiac function features from the medical image sequence by encoding pairs of images of the medical image sequence into the cardiac function features using a machine learning based feature extractor network;
   extracting additional features from patient data of the patient; and
   predicting a patient specific risk of a cardiac event based on the extracted cardiac function features and the extracted additional features.

2. The method of claim 1, wherein predicting a patient specific risk of a cardiac event based on the extracted cardiac function features comprises:
   determining a risk score representing the patient specific risk of the cardiac event.

3. The method of claim 2, wherein predicting a patient specific risk of a cardiac event based on the extracted cardiac function features comprises:
   classifying the patient specific risk of the cardiac event based on the risk score.

4. The method of claim 1, wherein extracting additional features from patient data of the patient comprises:
   encoding the patient data of the patient into the additional features using one or more additional machine learning based feature extractor networks.

5. The method of claim 4, wherein predicting a patient specific risk of a cardiac event based on the extracted cardiac function features comprises:
   concatenating the cardiac function features and the additional features to form a feature vector; and
   encoding the feature vector to features representing the patient specific risk of the cardiac event using a machine learning based risk regression network.

6. The method of claim 5, further comprising:
   individually training the machine learning based feature extractor network, the one or more additional machine learning based feature extractor networks, and the machine learning based risk regression network.

7. The method of claim 5, further comprising:
   training the machine learning based feature extractor network, the one or more additional machine learning based feature extractor networks, and the machine learning based risk regression network together.

8. An apparatus comprising:
   means for receiving a medical image sequence of a heart of a patient;
   means for extracting cardiac function features from the medical image sequence by encoding pairs of images of the medical image sequence into the cardiac function features using a machine learning based feature extractor network;
   means for extracting additional features from patient data of the patient; and
   means for predicting a patient specific risk of a cardiac event based on the extracted cardiac function features and the extracted additional features.

9. The apparatus of claim 8, wherein the means for predicting a patient specific risk of a cardiac event based on the extracted cardiac function features comprises:
   means for determining a risk score representing the patient specific risk of the cardiac event.

10. The apparatus of claim 9, wherein the means for predicting a patient specific risk of a cardiac event based on the extracted cardiac function features comprises:
    means for classifying the patient specific risk of cardiac events based on the risk score.

11. A non-transitory computer readable medium storing computer program instructions, the computer program instructions when executed by a processor cause the processor to perform operations comprising:
    receiving a medical image sequence of a heart of a patient;
    extracting cardiac function features from the medical image sequence by encoding pairs of images of the medical image sequence into the cardiac function features using a machine learning based feature extractor network;
    extracting additional features from patient data of the patient; and
    predicting a patient specific risk of a cardiac event based on the extracted cardiac function features and the extracted additional features.

12. The non-transitory computer readable medium of claim 11, wherein predicting a patient specific risk of a cardiac event based on the extracted cardiac function features comprises:
    determining a risk score representing the patient specific risk of the cardiac event.

13. The non-transitory computer readable medium of claim 11, wherein extracting additional features from patient data of the patient comprises:
    encoding the patient data of the patient into the additional features using one or more additional machine learning based feature extractor networks.

14. The non-transitory computer readable medium of claim 13, wherein predicting a patient specific risk of a cardiac event based on the extracted cardiac function features comprises:
    concatenating the cardiac function features and the additional features to form a feature vector; and
    encoding the feature vector to features representing the patient specific risk of the cardiac event using a machine learning based risk regression network.

15. The non-transitory computer readable medium of claim 14, further comprising:
    individually training the machine learning based feature extractor network, the one or more additional machine learning based feature extractor networks, and the machine learning based risk regression network.

16. The non-transitory computer readable medium of claim 14, further comprising:
    training the machine learning based feature extractor network, the one or more additional machine learning based feature extractor networks, and the machine learning based risk regression network together.

* * * * *